US 11,786,116 B2

(12) United States Patent
Wang et al.

(10) Patent No.: US 11,786,116 B2
(45) Date of Patent: Oct. 17, 2023

(54) MULTIPLE SOURCE ENDOSCOPY ILLUMINATION SYSTEM WITH ADJUSTABLE ANGULAR DISTRIBUTION AND WIDE FIELD OF VIEW

(71) Applicant: Excelitas Canada, Inc., Vaudreuil-Dorion (CA)

(72) Inventors: Yong Wang, Markham (CA); Sola Anne Kuk, Toronto (CA)

(73) Assignee: Excelitas Canada, Inc., Vaudreuil-Dorion (CA)

( * ) Notice: Subject to any disclaimer, the term of this patent is extended or adjusted under 35 U.S.C. 154(b) by 0 days.

(21) Appl. No.: 17/507,100

(22) Filed: Oct. 21, 2021

(65) Prior Publication Data
US 2022/0117477 A1   Apr. 21, 2022

Related U.S. Application Data

(60) Provisional application No. 63/094,388, filed on Oct. 21, 2020.

(51) Int. Cl.
*A61B 1/06* (2006.01)
*A61B 1/07* (2006.01)

(52) U.S. Cl.
CPC .......... *A61B 1/0684* (2013.01); *A61B 1/0638* (2013.01); *A61B 1/0676* (2013.01); *A61B 1/07* (2013.01)

(58) Field of Classification Search
CPC . A61B 1/00096; A61B 1/00163; A61B 1/046; A61B 1/0638; A61B 1/0676; A61B 1/0684; A61B 1/07; G02B 23/10; G02B 23/2407
See application file for complete search history.

(56) References Cited

U.S. PATENT DOCUMENTS

| | | | |
|---|---|---|---|
| 6,718,088 B2 | 4/2004 | Okazaki et al. | |
| 7,502,176 B2 | 3/2009 | Mino et al. | |
| 8,472,765 B2 | 6/2013 | Holland et al. | |
| 8,967,846 B2 | 3/2015 | Jaffe et al. | |
| 2002/0026099 A1* | 2/2002 | Adachi | A61B 1/00009 600/178 |
| 2005/0047172 A1* | 3/2005 | Sander | G02B 21/06 362/555 |
| 2006/0274434 A1 | 12/2006 | Mino et al. | |
| 2011/0112377 A1* | 5/2011 | Papac | A61B 3/12 600/249 |

(Continued)

*Primary Examiner* — Aaron B Fairchild
*Assistant Examiner* — Julianna J Nicolaus
(74) *Attorney, Agent, or Firm* — Wolf, Greenfield & Sacks, P.C.

(57) ABSTRACT

An illumination system for an endoscope has a plurality of light assemblies, including a red assembly with a red light source, a blue assembly with a blue light source, a green assembly with a green light source, and an infrared (IR) assembly with an IR light source. Each light assembly further includes an output beam shape adjuster configured to receive an output beam from the respective light source and adjust the beam angular profile, and an output beam angle adjuster configured to receive a beam from the output beam shape adjuster and adjust the output beam angle. A plurality of dichroic plates are configured to combine output beams of the red assembly, the blue assembly, the green assembly, and the IR assembly.

21 Claims, 19 Drawing Sheets

(56) References Cited

U.S. PATENT DOCUMENTS

| | | | |
|---|---|---|---|
| 2016/0076735 A1* | 3/2016 | Wang | G01N 21/6456 |
| | | | 362/84 |
| 2016/0380410 A1* | 12/2016 | Song | G02B 27/10 |
| | | | 359/639 |
| 2018/0275416 A1 | 9/2018 | Wang et al. | |
| 2019/0011365 A1* | 1/2019 | Ge | G02B 21/0076 |
| 2019/0121146 A1 | 4/2019 | Wang et al. | |
| 2021/0076921 A1* | 3/2021 | Nagae | A61B 1/0638 |

* cited by examiner

MULTIPLE SOURCE ENDOSCOPY ILLUMINATION SYSTEM WITH ADJUSTABLE ANGULAR DISTRIBUTION AND WIDE FIELD OF VIEW

CROSS-REFERENCE TO RELATED APPLICATIONS

This application claims the benefit of U.S. Provisional Patent Application Ser. No. 63/094,388, filed Oct. 21, 2020, entitled "Multiple source endoscopy illumination system with adjustable angular distribution and Wide Field of View," which is incorporated by reference herein in its entirety.

FIELD OF THE INVENTION

The present invention relates to illumination systems, and more particularly, is related to an endoscopy light source.

BACKGROUND OF THE INVENTION

LED and laser based illumination for life science and medical applications has developed dramatically over recent years. Microscopy and endoscopy are two applications that demand increasing performance from the light source for improved quantitative analysis. For most applications, a fiber bundle is used to deliver light from the light source to the illumination target. Typically, such a fiber bundle has a small diameter, for example, 1-3 mm to provide sufficient light intensity while meeting small space limitations. Such illumination systems typically have:
1. A wide field of view fiber bundle: Most endoscope fiber bundles have a full field of view of 64-80 degrees.
2. An illumination source combining multiple color LEDs or lasers, for example, Red, Blue, Green/Yellow and an infrared (IR) source. More recently, some illumination systems have used laser light for all spectral bands combining three to six visible laser wavelengths as well as one or more IR laser wavelengths. Some applications involve additional visible colors such as Cyan or non-visible wavebands such as ultraviolet (UV). Each of these variations demand uniform angular color distribution, preferably having a deviation between colors less than ±4-5% within whole field of view.
3. For recent advancements in robotics, micro-instrumentation, and endoscope design, IR light sources are used for tissue fluorescence analysis. It is desirable to match the angular distribution of the IR source to the white light source typically consisting of Red, Green and Blue light sources with a variation less than 5%.
4. Reduced variation of the output beam may improve quantitative image analysis.

Traditionally, dichroic plates are used to combine LEDs or laser beams with different wavelengths, as described in patent literature, for example U.S. Pat. No. 8,967,846 B2, US 2016/0076735, US 2018/0275416, and US 2019/0121146. However, even among these examples the beam angular distribution of the system output is varied. These variations result from combining different light sources together to make up the systems optical output. The individual light source components all have different angular distributions and when combined their beam profiles do not overlap. Fundamentally, each type of source laser or LED emit radiation with different spatial and angular profiles. Even light sources with similar light emitting structures have different beam profiles for different emitting wavelengths.

Due to their multi-mode nature, the variation of the angular distribution of the lasers may be much greater than LEDs. It is a challenge for current fixed optical path illumination systems to achieve beam angular distribution within desired tolerances for endoscope illumination applications, for example, deviation between colors less than 4-5% within a 40 degree field of view. Therefore, there is a need in the industry to address one or more of these shortcomings.

SUMMARY OF THE INVENTION

Embodiments of the present invention provide a multiple source endoscopy illumination system with adjustable angular distribution and a wide field of view. Briefly described, the present invention is directed to an illumination system for an endoscope with a plurality of light assemblies. The assemblies include a red assembly with a red light source, a blue assembly with a blue light source, a green assembly with a green light source, and an infrared (IR) assembly with an IR light source. Each light assembly further includes an output beam shape adjuster configured to receive an output beam from the respective light source and adjust the beam angular profile, and an output beam angle adjuster configured to receive a beam from the output beam shape adjuster and adjust the output beam angle. A plurality of dichroic plates are configured to combine output beams of the red assembly, the blue assembly, the green assembly, and the IR assembly.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principals of the invention.

DETAILED DESCRIPTION

Figure 1:
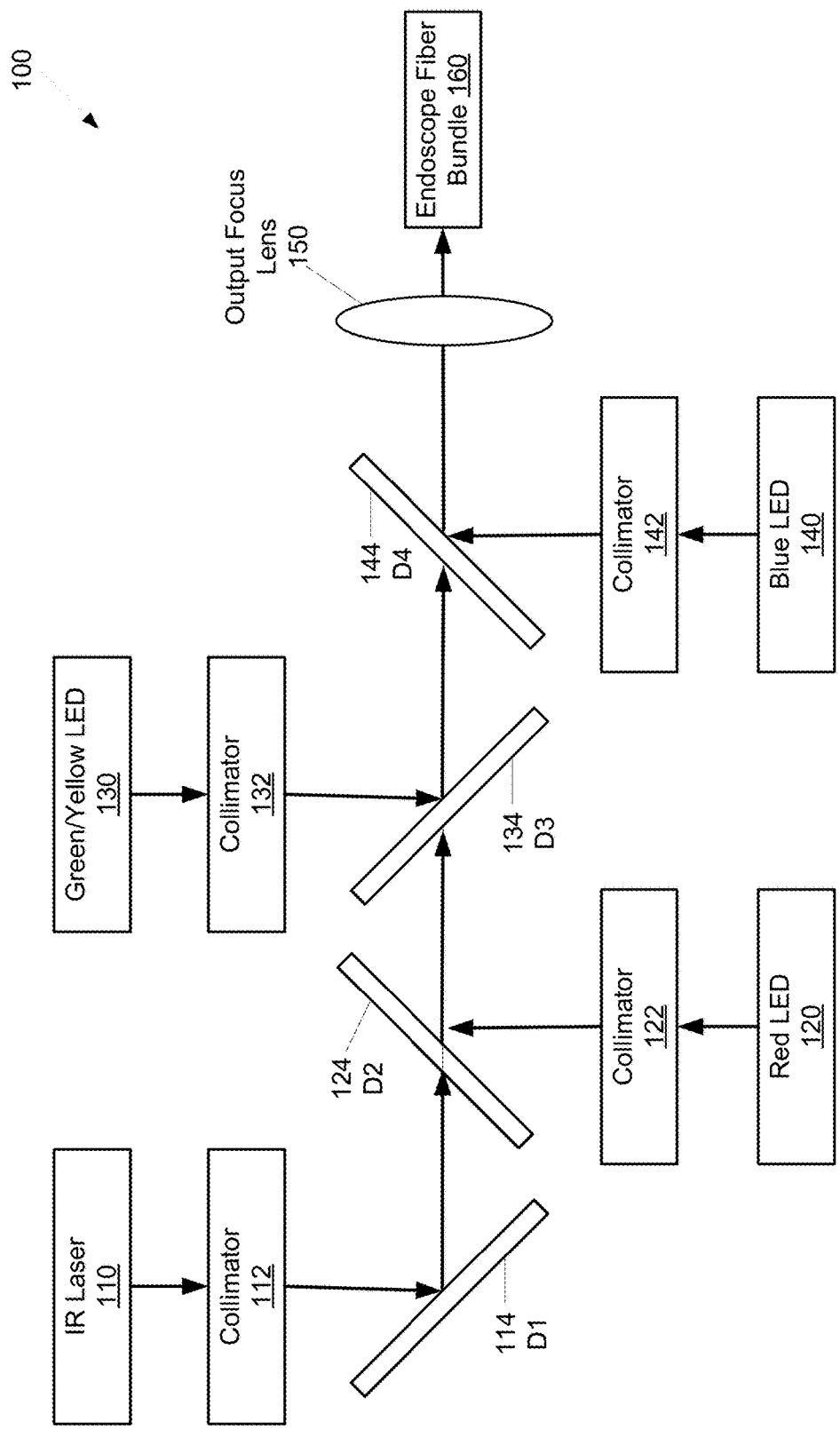
FIG. 1 is a schematic diagram showing a prior art endoscope illumination source.

The following definitions are useful for interpreting terms applied to features of the embodiments disclosed herein, and are meant only to define elements within the disclosure.

As used within this disclosure, a "dichroic plate" is an interference filter that is a very accurate color filter used to selectively pass light of a small range of colors while reflecting other colors.

As used within this disclosure, a "beam localizer" is an optical device that converts received input optical beams with different axial locations and beam widths to an output beam with same beam central location and same beam width for different colors as desired.

As used within this disclosure, a "channel output beam shape adjuster" is an optical device that adjusts one or more parameters of an optical element in a system to redistribute the input light to a desired angular profile of an output beam.

As used within this disclosure, a "beam angle adjuster" is an optical device that adjusts one or more parameters of an optical element in a system to adjust the output beam angle.

Reference will now be made in detail to embodiments of the present invention, examples of which are illustrated in the accompanying drawings. Wherever possible, the same reference numbers are used in the drawings and the description to refer to the same or like parts.

As described above in the background section, a conventional endoscope illumination system 100 as shown by FIG. 1 combines LED and IR laser light with different wavelengths, for example Red LED (610-650 nm), Blue LED (430-470 nm) Green/yellow LED (515-600 nm), and IR laser (785-800 nm). A first collimator 112 collimates light from an IR laser 110, and a first dichroic plate 114 directs the collimated IR light toward an output focus lens 150. A second collimator 122 collimates light from a red LED 120 toward a second dichroic plate 124, where the second dichroic plate 124 combines the red collimated light with the IR collimated light. A third collimator 132 collimates light from a green/yellow LED 130 toward a third dichroic plate 134, where the third dichroic plate 134 combines the green/yellow collimated light with the combined red and IR light. A fourth collimator 142 collimates light from a blue LED 140 toward a fourth dichroic plate 144, where the fourth dichroic plate 144 combines the blue collimated light with the combined red, yellow/green and IR light. The output focus lens 150 focuses the combined red, green/yellow, blue, and IR light into an endoscopic fiber bundle 160.

Figure 2:
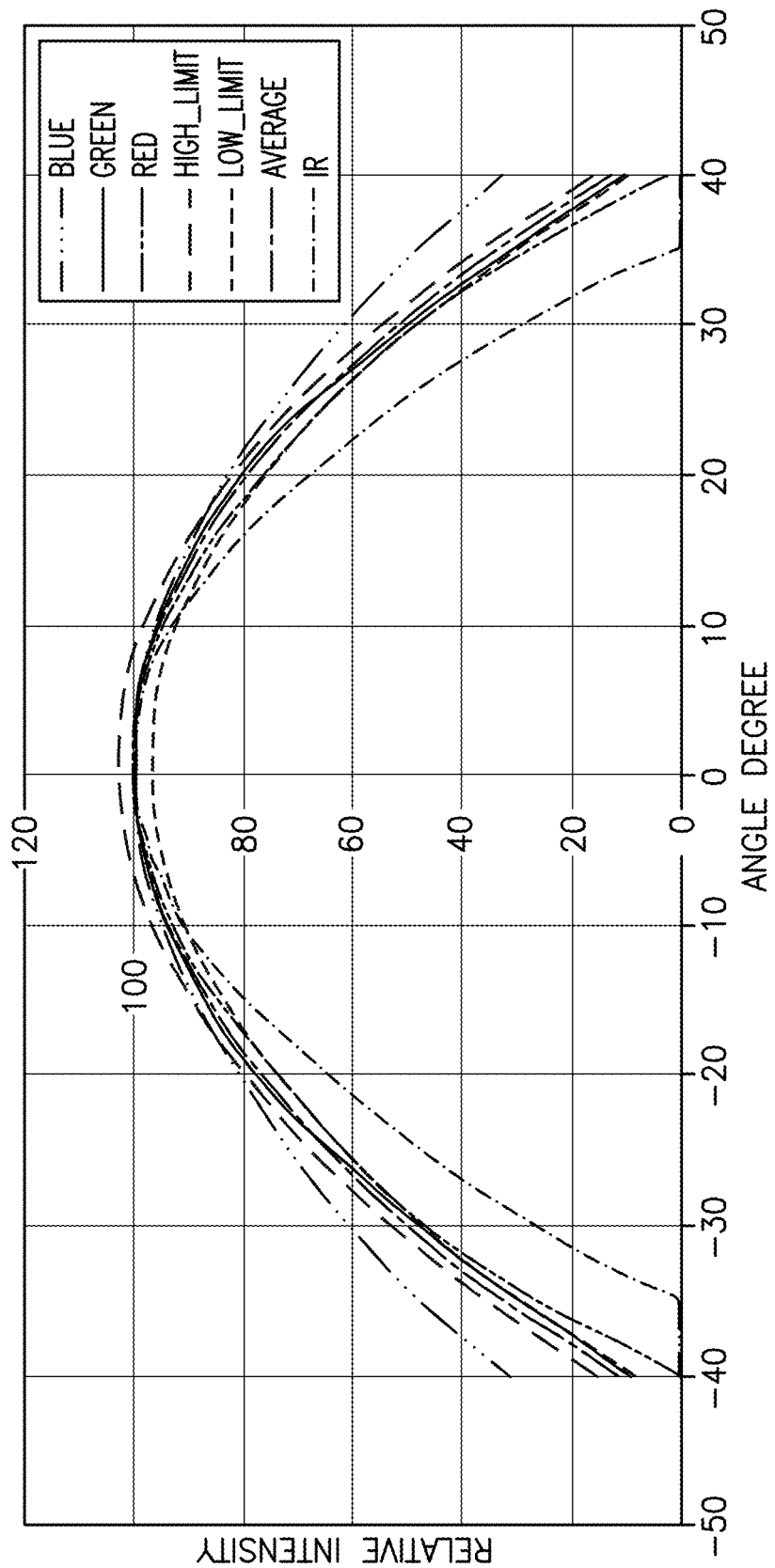
FIG. 2 is a plot of the output beam profile of the endoscope illumination source of FIG. 1.
Figure 3:
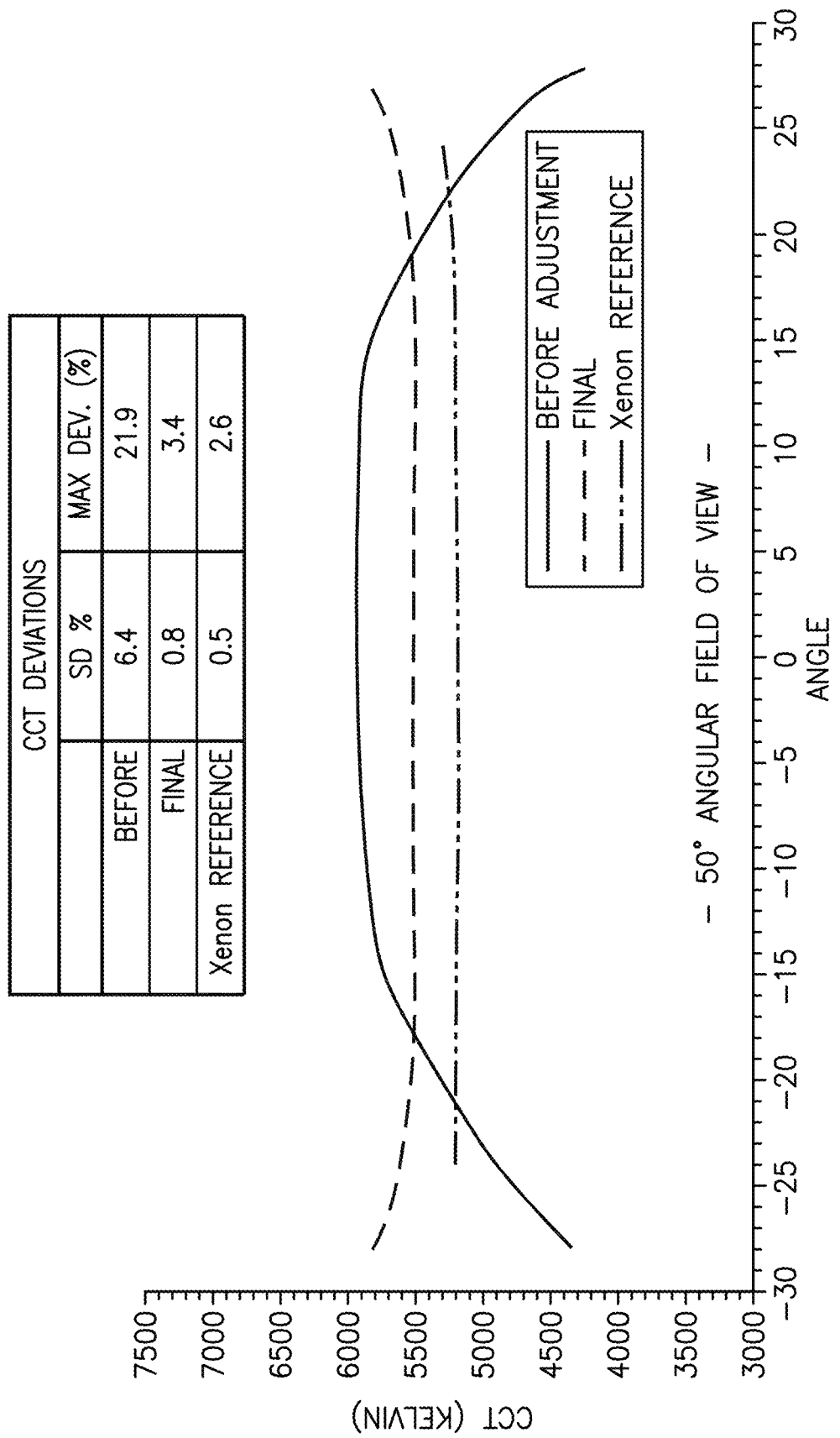
FIG. 3 is a plot of the color correlated temperature (CCT) of the endoscope illumination source of FIG. 1 before and after adjusting the angular distribution.

As shown by FIG. 2, the beam profile at the output of the endoscope system 100 has an undesirably large variation. Likewise, in many cases the output beam angular distribution exceeds the high and low limitation for a given application. This angular distribution is directly related to the color uniformity. One important parameter of the color uniformity is the color correlated temperature (CCT) of the illumination field, as shown by FIG. 3. The "before" row in the CCT Deviations row indicates the output beam angular distribution of the system of FIG. 1, while the "Final" row indicates the output beam angular distribution of the system of FIG. 6. Here the CCT variation of the field is dramatically improved from 22% to 3.4% before and after adjusting the angular distribution, as described further below. The uniform Xenon beam is shown as an ideal case for reference.

Figure 4:
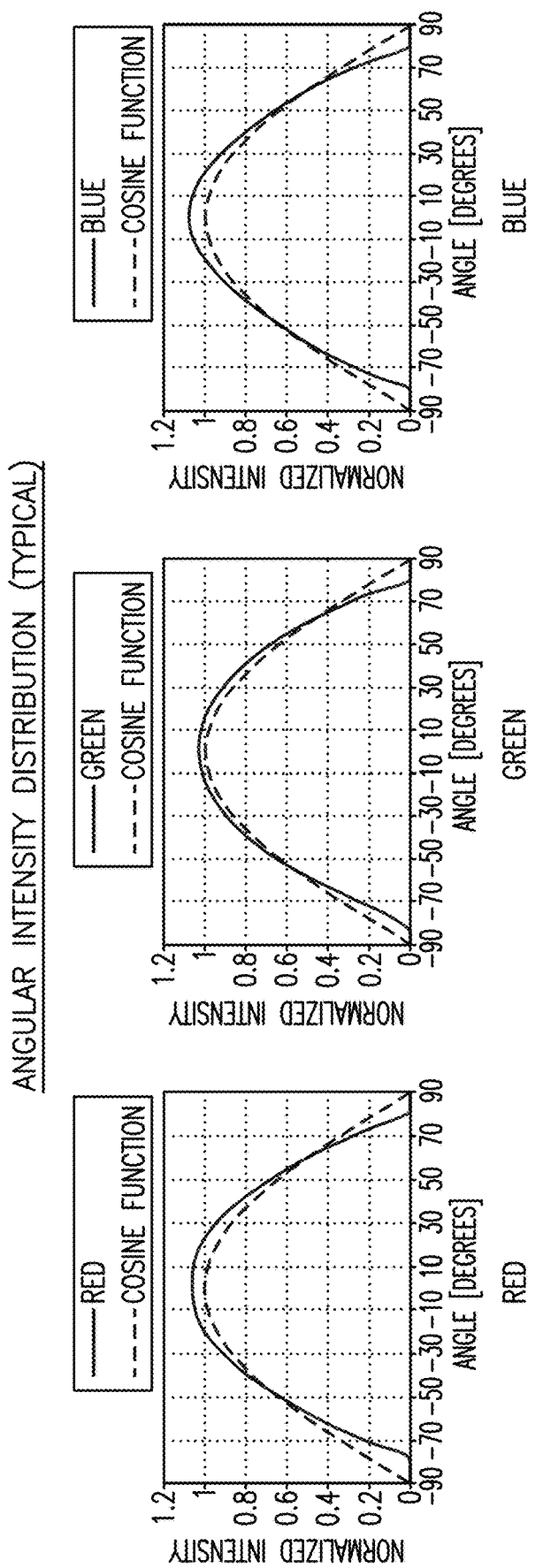
FIG. 4 shows plots of angles for red, green/yellow, and blue LEDs from the same supplier.

The individual light sources, red 120, green/yellow 130, and blue 140 LEDs and the IR laser 110 have different angular distribution for many reasons. First, LEDs and laser diodes employ different semiconductor materials to emit light at different wavelengths, which impacts the efficiency and light distribution. Second, each laser or LED technology utilizes different electro-optical architectures for generating and extracting light producing varied optical powers, sources sizes and beam shapes. Finally, each manufacturer has their own proprietary semiconductor packaging technology that also impacts the light distribution. FIG. 4 shows one example of the angular distribution for the red LED 120, green/yellow LED 130, and the blue LED 140 from same manufacturer.

Figure 5:
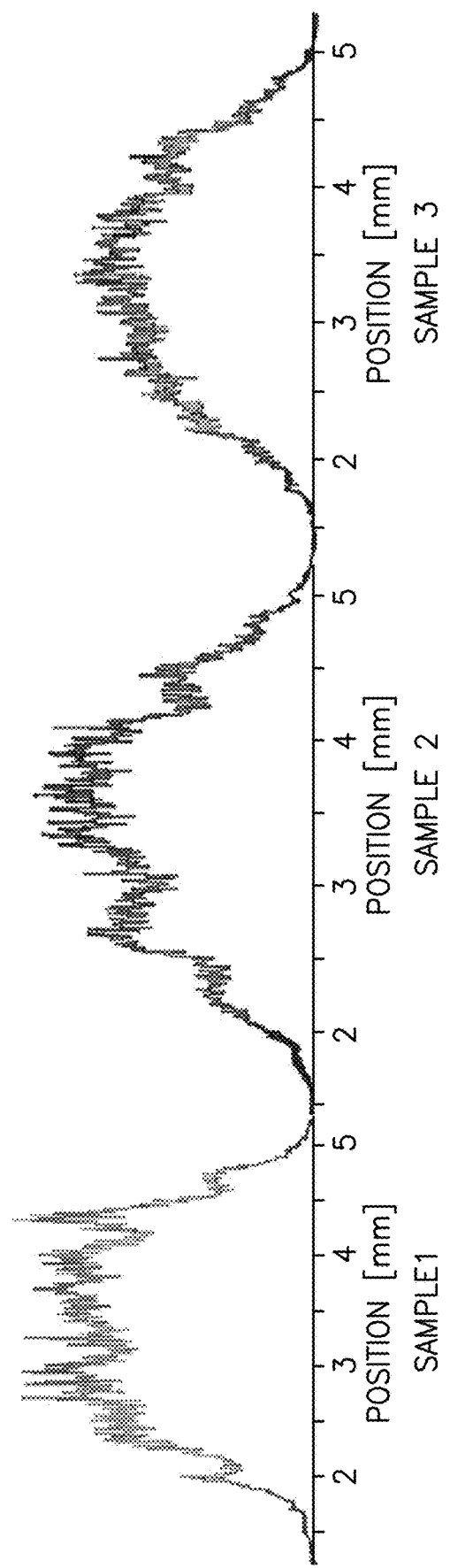
FIG. 5 shows angular distribution plots of three sample lasers with same 785 nm wavelength.

Even different LEDs or lasers of the same wavelength may have different angular distributions, as shown in FIG. 5 by the plots of three samples of laser with same wavelength of 785 nm. Differences in the packaging of lasers may also impact the output beam angular distribution. Further, optics in an optical path, for example collimators, focus lenses and the endoscope fiber bundle typically have different refractive indexes for different colors.

Figure 6:
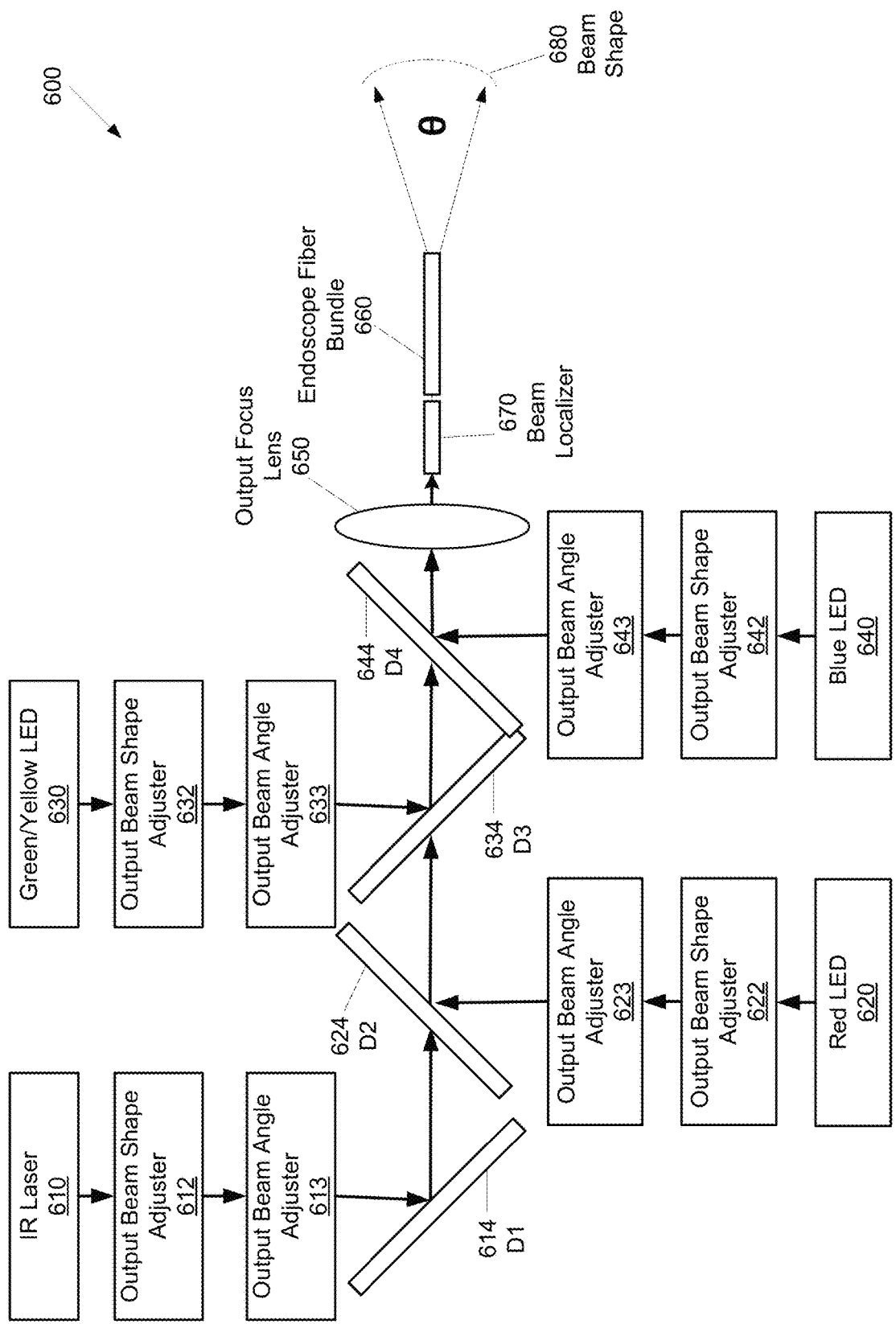
FIG. 6 is a schematic diagram of an exemplary embodiment of an endoscope illumination source.

FIG. 6 is a schematic diagram of a first exemplary embodiment of an endoscope light source 600. Under the first exemplary embodiment, the light source 600 includes an IR laser 610, a red LED 620, a green/yellow LED 630, and a blue LED 640. An output beam angle Θ is adjusted by using individual beam angle adjusters 613, 623, 633, 643 respectively for each of the IR laser 610, the red LED 620, the green/yellow LED 630, and the blue LED 640. The output beam angular profile is adjustable using individual beam shape adjusters 612, 622, 632, 642 respectively for each of the IR laser 610, the red LED 620, the green/yellow LED 630, and the blue LED 640.

An IR laser assembly includes the IR laser 610, a first output beam shape adjuster 612 that receives light from the IR laser 610, and a first output beam angle adjuster 613 that receives light from the first output beam shape adjuster 612. A first dichroic plate 614 directs the beam angular profile and angle adjusted light toward an output focus lens 650 via a second dichroic plate 624.

A red LED assembly includes a red LED 620, a second output beam shape adjuster 622 that receives light from the red LED 620, and a second output beam angle adjuster 623 that receives light from the second output beam shape adjuster 622. the second dichroic plate 624 combines the beam angular profile and angle adjusted red light with and the beam angular profile and angle adjusted IR light and directs the combined light toward the output focus lens 650 via a third dichroic plate 634.

A green/yellow LED assembly includes a green/yellow LED 630, a third output beam shape adjuster 632 that receives light from the green/yellow LED 630, and a third output beam angle adjuster 633 receives light from the third output beam shape adjuster 632. The third dichroic plate 634 combines the beam angular profile and angle adjusted green/yellow light with the beam angular profile and angle adjusted red light and the beam angular profile and angle adjusted IR light and directs the combined light toward the output focus lens 650 via a fourth dichroic plate 644.

A blue LED assembly includes a blue LED 640, a fourth output beam shape adjuster 642 that receives light from the blue LED 640, and a fourth output beam angle adjuster 643 that receives light from the fourth output beam shape adjuster 642. The fourth dichroic plate 644 combines the beam angular profile and angle adjusted blue light with the beam angular profile and angle adjusted green/yellow light, the beam angular profile and angle adjusted red light, and the beam angular profile and angle adjusted IR light and directs the combined light toward the output focus lens 650.

Figure 7:
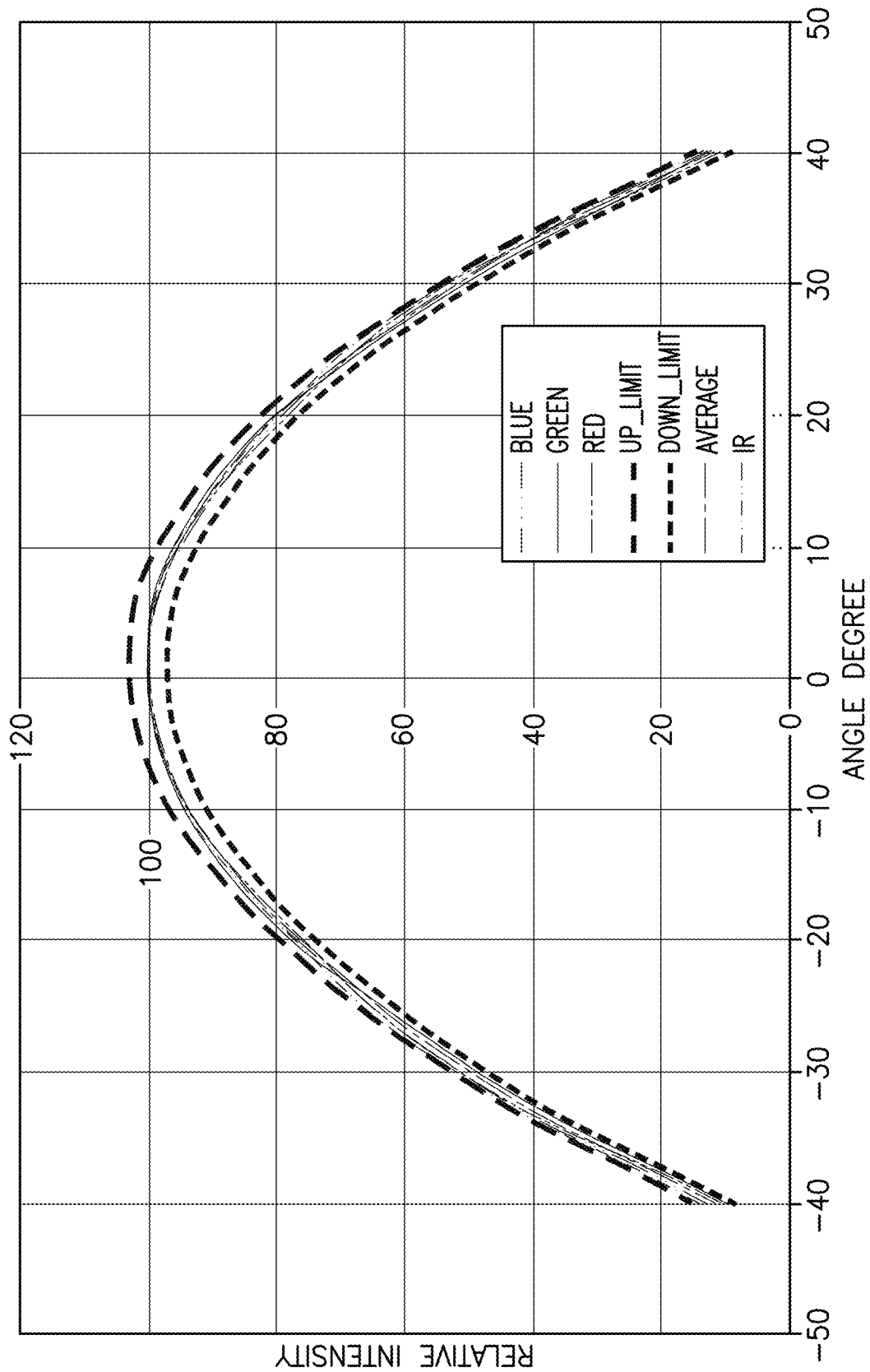
FIG. 7 is a plot of the output beam profile of the endoscope illumination source of FIG. 6.

An output beam localizer 670 receives the output of the output focus lens 650 and controls the location, point angle, and beam width of the output beam such that the new tolerance is defined by the mechanical dimension of the localizer (for example pointing angle<0.5 degrees, beam width position +/−25 um and beam waist location +/−25 um). The beam localizer 670 may be, for example, a hexagonal shape homogenizing rod with a hexagonal profile shape, a rectangle profile shape, or another polygon shaped homogenizing rod or taper. The output of the beam localizer 670 is coupled into the endoscope fiber bundle 660. FIG. 7 is a plot of the output beam profile of the first exemplary embodiment endoscope illumination source.

Figure 8A:
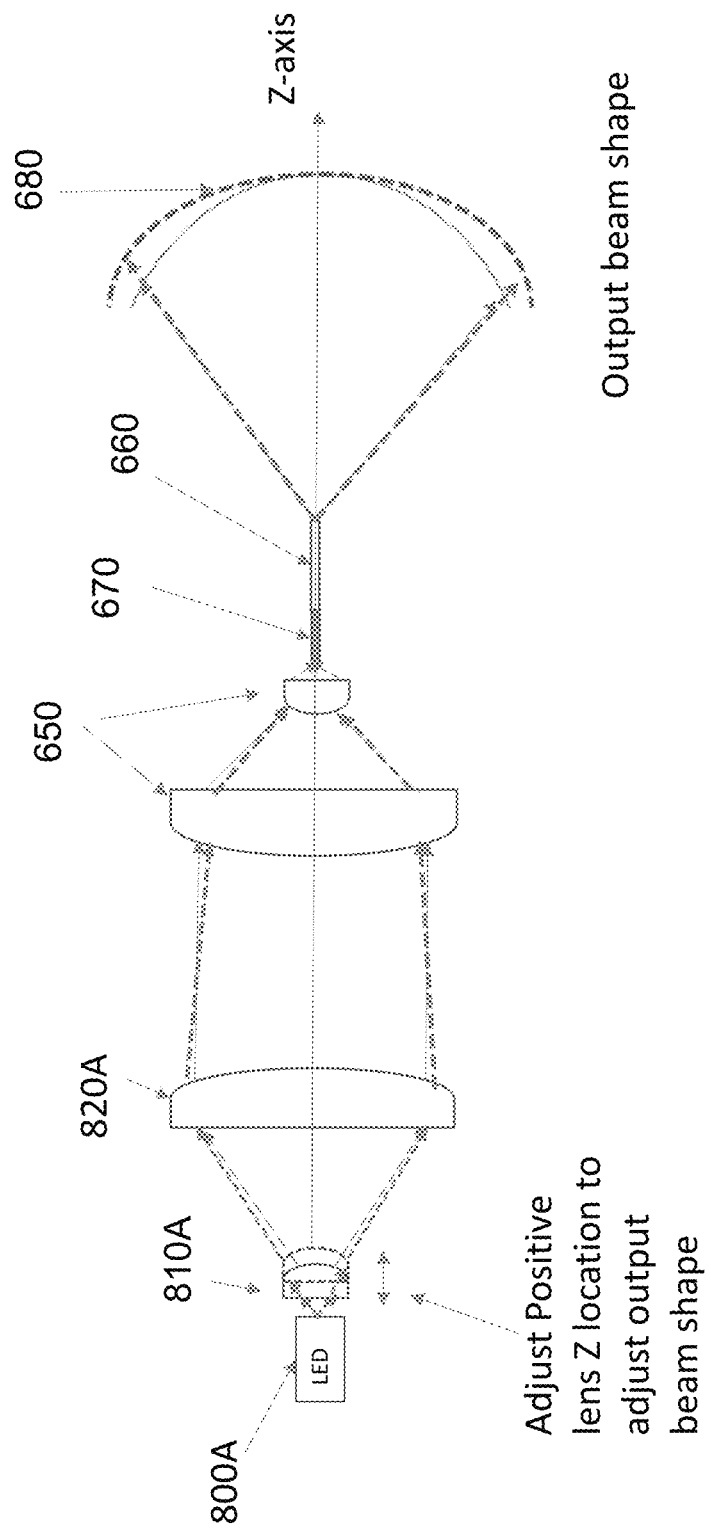
FIG. 8A is a schematic diagram showing a LED beam shape adjuster of FIG. 6 with a an adjustable positive lens location.
Figure 8B:
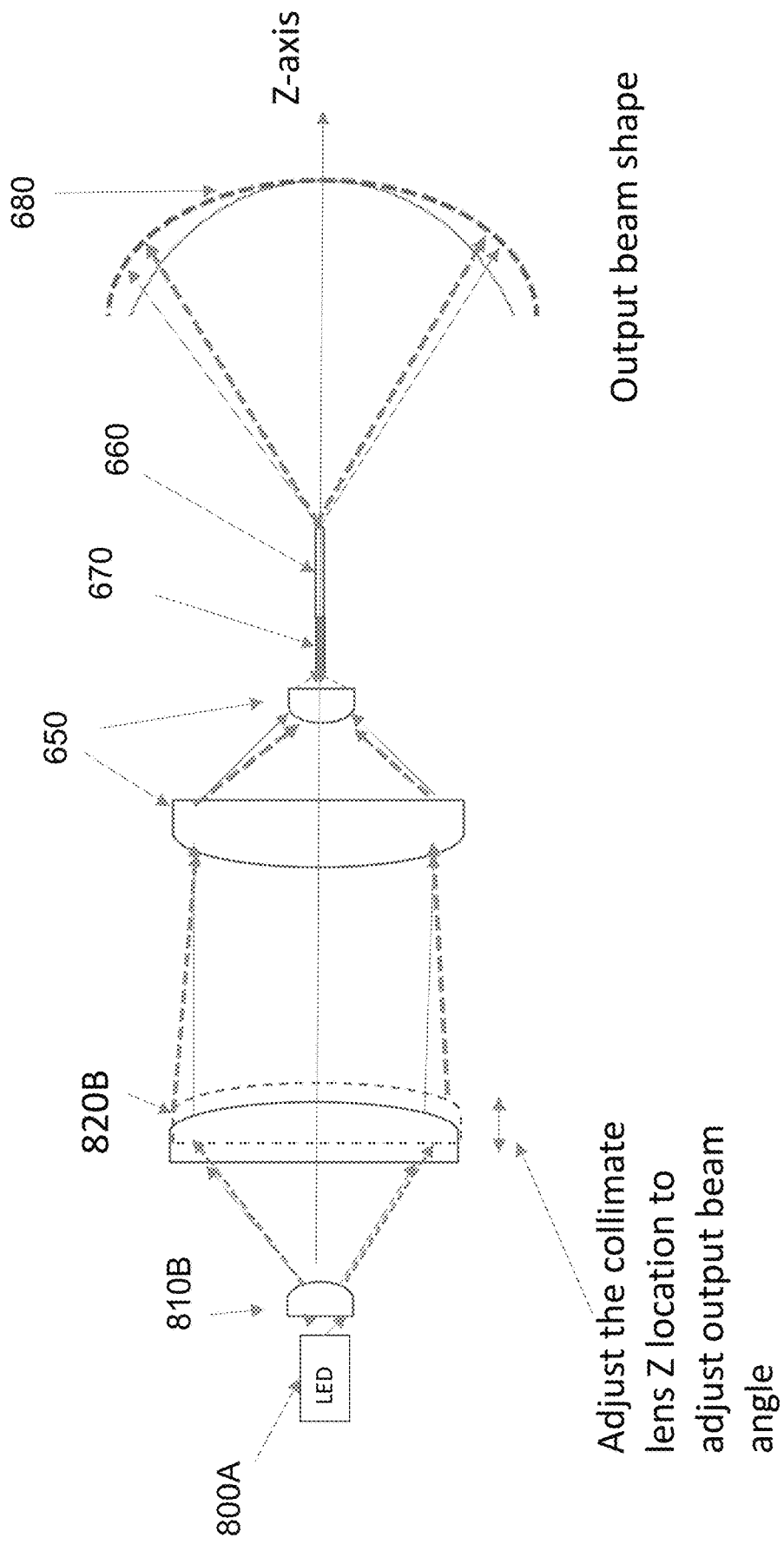
FIG. 8B is a schematic diagram showing a LED beam angle adjuster of FIG. 6 with a an adjustable positive lens location.

The principle of the beam shaping adjusters 612, 622, 632, 642 is described further here. As shown by FIG. 8A, the output angle of an LED light source 800A is relatively wide. In FIG. 8A, the LED 800A has an output with a field of view (FOV) of about 120 degrees. The collection lens 810A, which may be a positive lens, is used as a beam shape adjustor by adjusting the Z direction location of the collection lens 810A with respect to the LED 800A. In FIG. 8B, a movable collimating lens 820B is used as a beam angle adjustor by adjusting the Z direction location of the collimating lens 820B.

Each of the output LED beam shape adjusters 622, 632, 642 may include a location adjustable positive lens 810A or a location adjustable negative lens 1010A (See FIG. 10A), and/or an adjustable scattering cone opening diameter.

Figure 9:
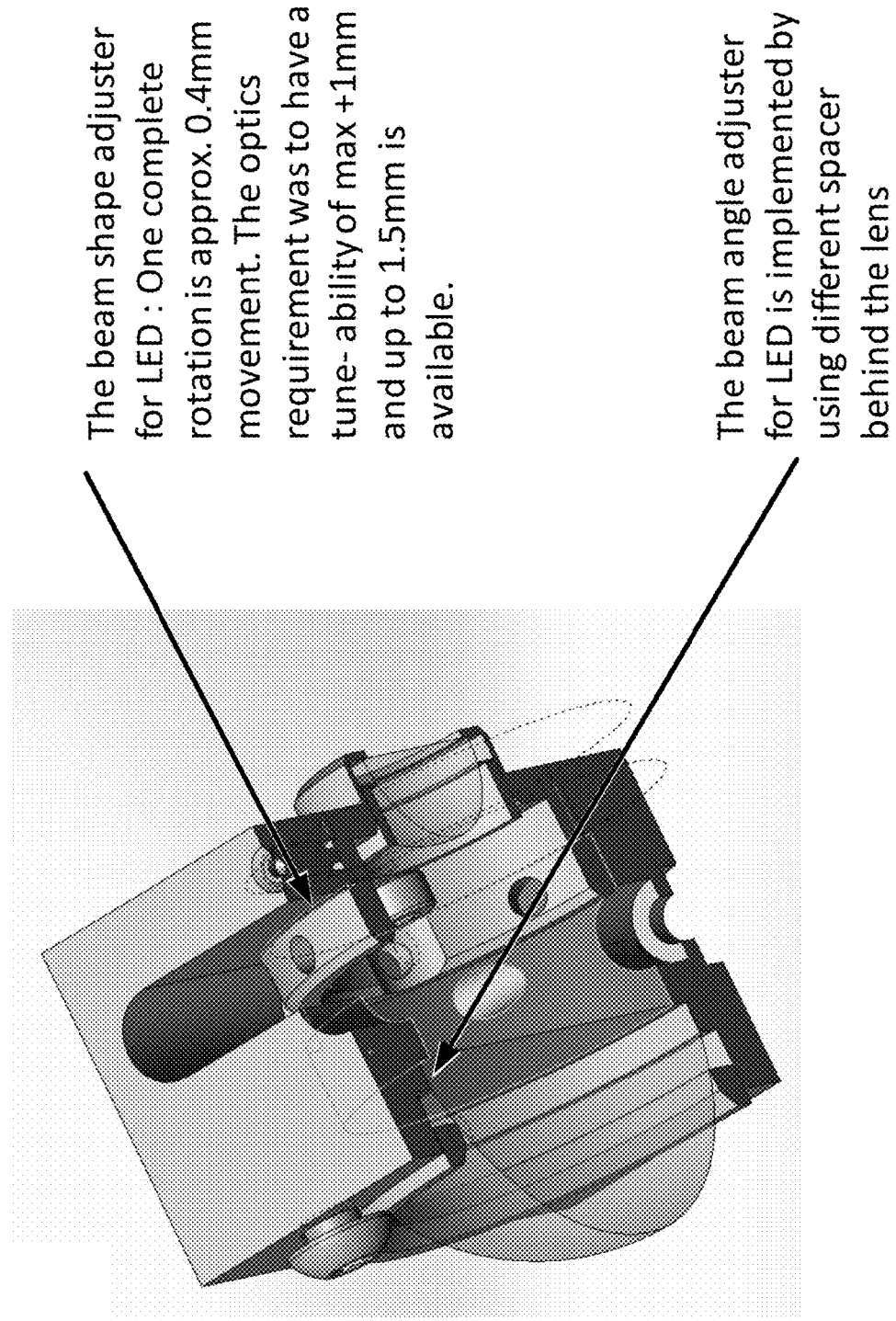
FIG. 9 is a schematic diagram is a schematic diagram showing the mechanical structure of the beam shape adjuster and beam angle adjuster of FIG. 8A.

For each of the output LED beam shape adjusters 622, 632, 642, the output beam shaping adjusting element normally is positive lens with an adjustable z axis location. By adjusting a first collection lens location, the output beam angular profile can be adjusted. All three LEDs: Red, Green and Red can be adjusted to within a specified angular distribution range, for example, ±4-5% within 40 degrees of full field of view. FIG. 9 shows a schematic diagram of the mechanical structure of the beam shape adjustor. The location of the shaping lens can be adjusted by a scaled turning wheel.

Figure 10A:
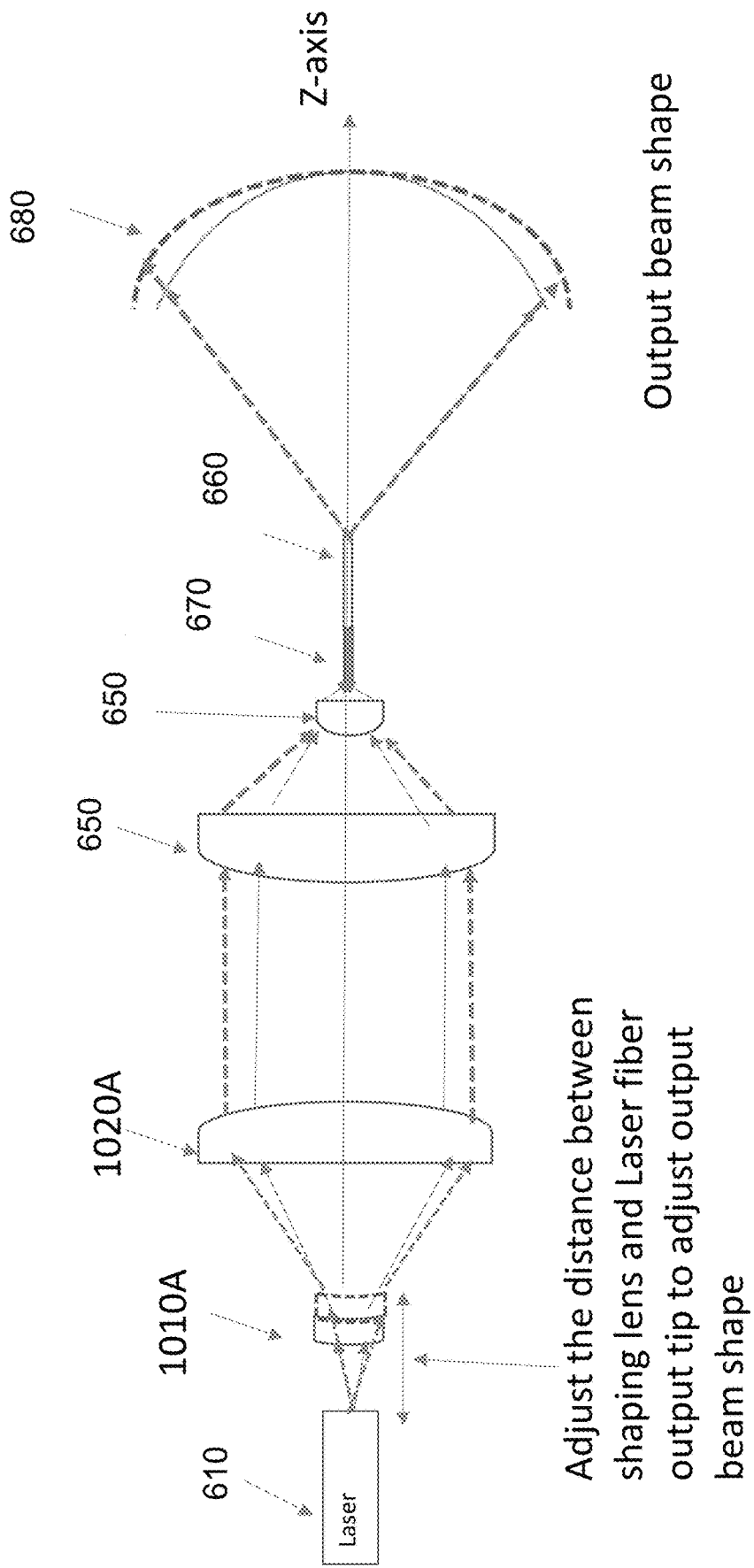
FIG. 10A is a schematic diagram showing a Laser beam shape adjuster of FIG. 6 with a an adjustable negative lens location.
Figure 10B:
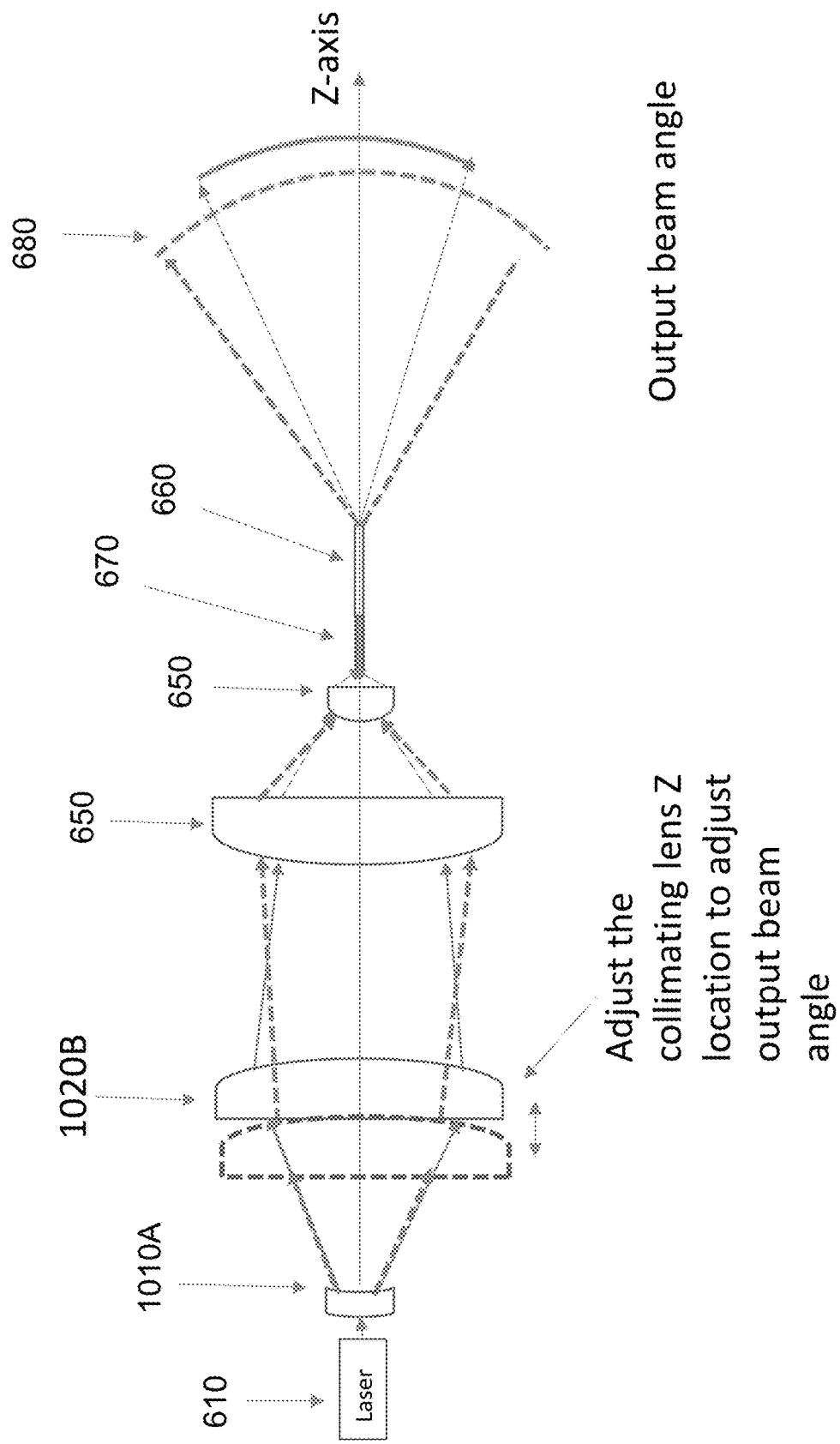
FIG. 10B is a schematic diagram showing a beam angle adjuster of FIG. 6.

In contrast with the LED, the angle of the laser light source 610 is relatively narrow, as shown by FIG. 10A. In FIG. 10A, a laser light source 610, has an output, for example, with about a 10-17 degree FOV. A beam shaping lens 1010A, typically a negative lens, is used as beam shape adjustor by adjusting the Z direction location of the beam shaping lens 1010A with respect to the laser source 610. In FIG. 10B a collimating lens 1020B is used as beam angle adjustor by adjusting the Z direction location of the collimating lens 1020B.

The output beam shaping adjust element normally is a negative lens 1010A with an adjustable z-axis location. The laser output beam shape is adjusted by changing the location of the negative lens 1010A along the z-axis.

As shown in FIGS. 8B and 10B, each of the output beam angle adjusters 613, 623, 633, 643 (FIG. 6) may include a location adjustable positive lens 820B, 1020B, and/or a location adjustable lens pair (positive and negative lens together). All laser output distribution angles have much greater variations, which without adjustment the output beam angle would have significant beam angular variations. The laser output angle can be adjusted by adjusting the location of the collimating lens 820B, 1020B.

Figure 10C:
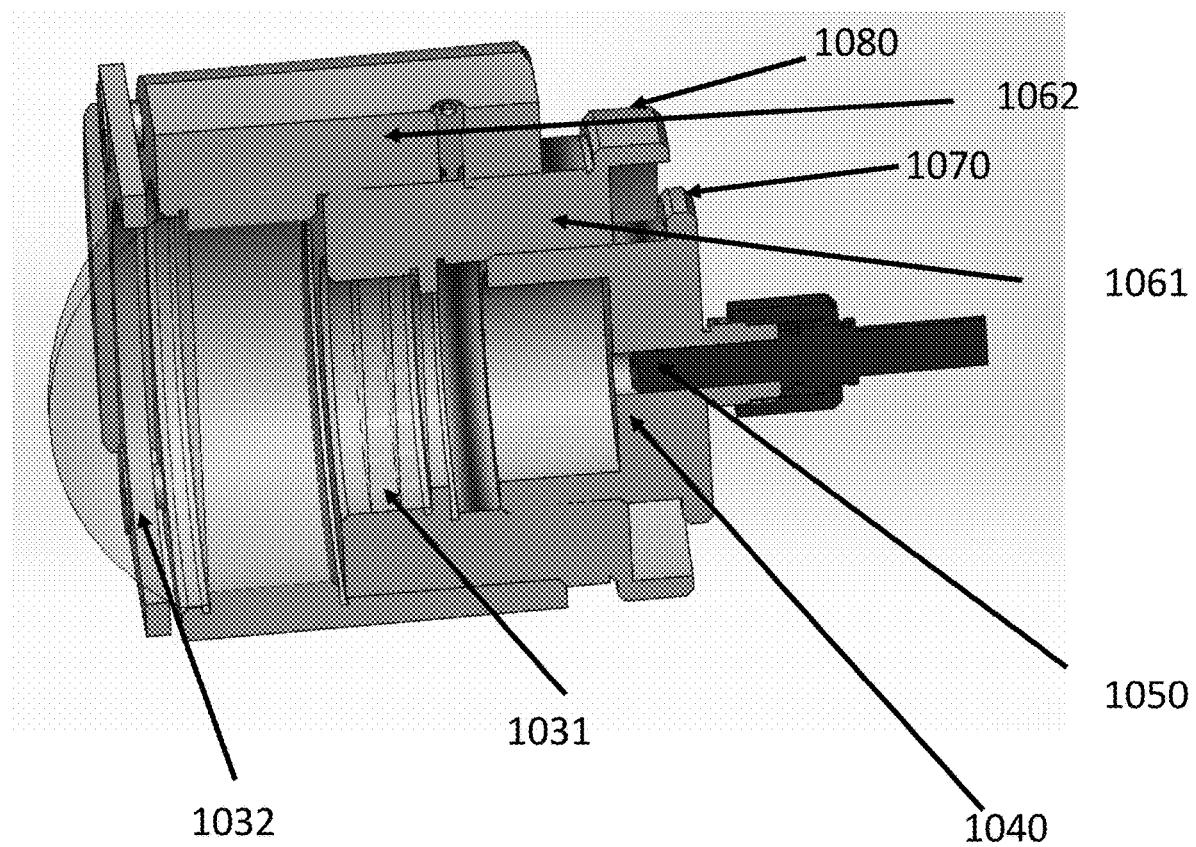
FIG. 10C shows the mechanical structure of the laser beam shape and angle adjuster sample for laser.

By adjusting the location of the beam angle adjuster 613, 623, 633, 643 (FIG. 6), and the beam shaping adjuster 612,622,632, 642, (FIG. 6) output beam angular distribution for all lasers can be adjusted to be within the application needs for illumination and color uniformity in the field of view (for example, for uniform illumination the intensity at the edge of the field of view should be no less than 40% of the center and each color should overlap within +/−4%). FIG. 10C shows the mechanical structure of the beam shape and angle adjuster sample for laser. The location of the adjuster can be adjusted for example, by a threaded tube. The shape adjuster consists of a first optical element 1031 (such as negative lens, positive lens, diffusing element), a second optical element 1032 and a receiving port 1040 for an optical fiber 1050. The first optical element 1031 has a first housing 1061 where the axial position relative to the receiving port 1040 can be tuned to adjust the beam shape. The second optical element 1032 has a second housing 1062 where the axial position relative to the first optical element 1031 can be adjusted to tune the angular distribution. An external mechanical mechanisms 1070 and 1080 tunes the position of the optical elements for in-situ real time monitoring.

There is an opto-mechanical component tolerance stack-up in every illumination system that is undesirable when coupling to smaller and smaller optical fibers. This tolerance stack-up leads to variation in the output beam position, beam waist and beam pointing angle relative to the endoscope fiber bundle 660. This variation affects the coupling efficiency to the fiber bundle and creates uncertainty in the output beam profile thus illumination quality cannot be maintained. The beam localizer 670 is inserted between light engine and fiber bundle to ensure consistent coupling to the fiber bundle.

Figure 11:
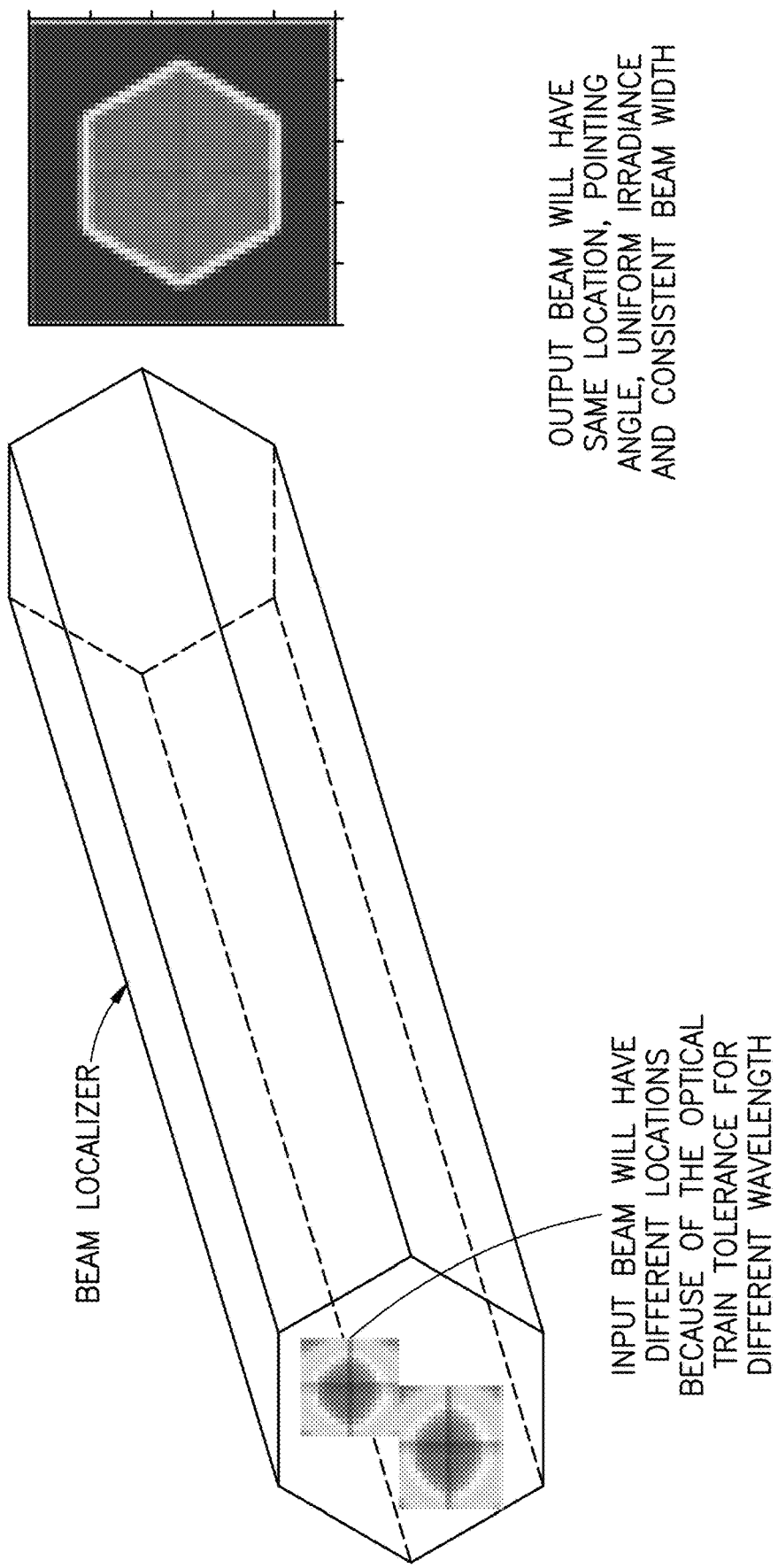
FIG. 11 is a schematic drawing of the beam localizer of FIG. 6.
Figure 12A:
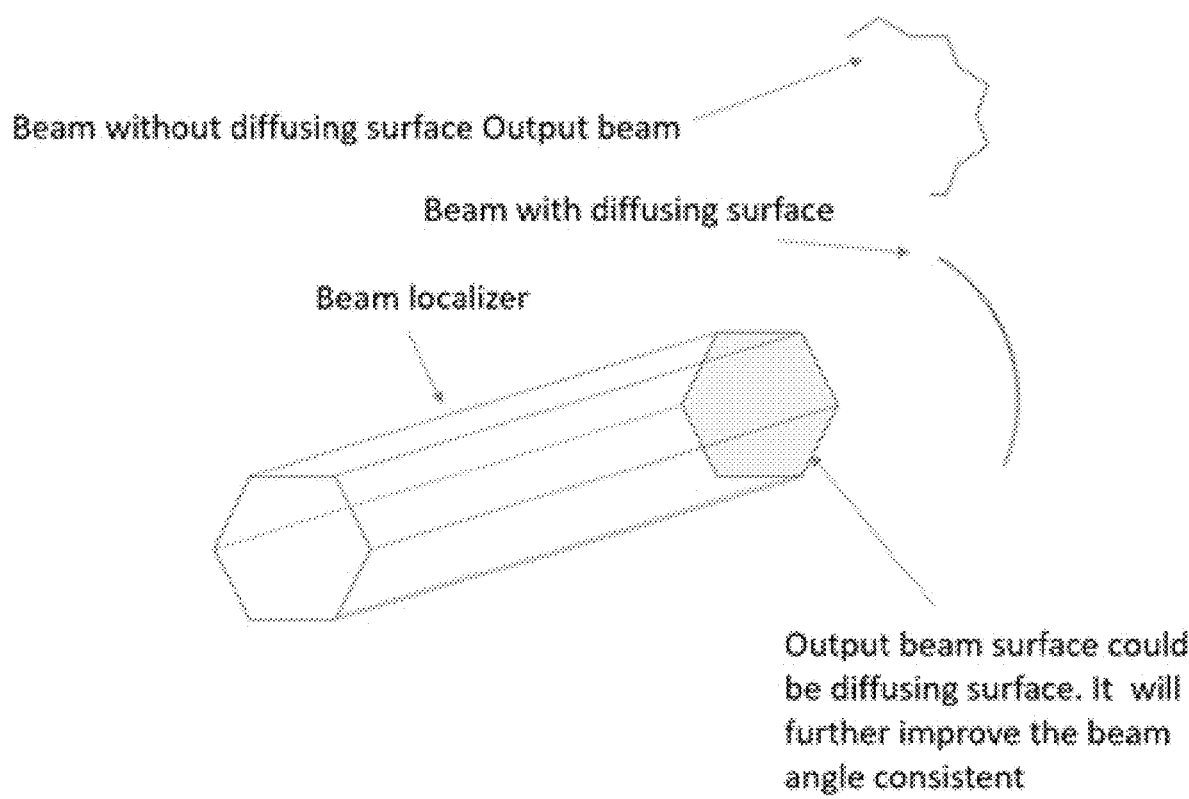
FIG. 12A is a schematic drawing of the beam localizer from a perspective view.
Figure 12B:
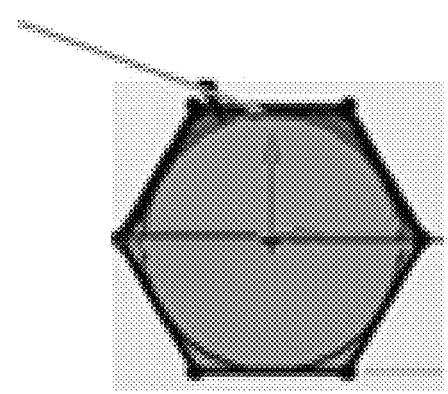
FIG. 12B is a schematic drawing of the beam localizer from a cross sectional view.

Under a first embodiment shown in FIG. 11, the beam localizer 670 is a homogenizing rod having a hexagonal cross-sectional shape. Alternatively, the beam localizer 670 may be a homogenizing rod having a rectangle shape or another polygon shaped cross-section. The beam localizer 670 dramatically improves the output beam quality including beam position, point angle and beam width. All these parameters may be controlled within a dimension tolerance range of the beam localizer 670. For example, the endoscope fiber bundle 660 may be in the range of 3-7 meters long and composed of hundreds of small core fibers with high numerical aperture, for example in the range of 0.5-0.7. The output angle distribution is mixed by the long fiber bundle 660. If the fiber bundle 660 is shorter than 3 meters, or the fiber bundle 660 is composed of larger core fibers, the output end surface of the beam localizer 670 could include a diffusing surface to further improve the beam angle distribution, as shown by FIG. 12A. FIG. 12B which depicts the mechanical structure of the beam localizer. The output beam location will be decided by the output end surface of the beam localizer, for example beam width variation is less than ±25 μm.

Figure 13:
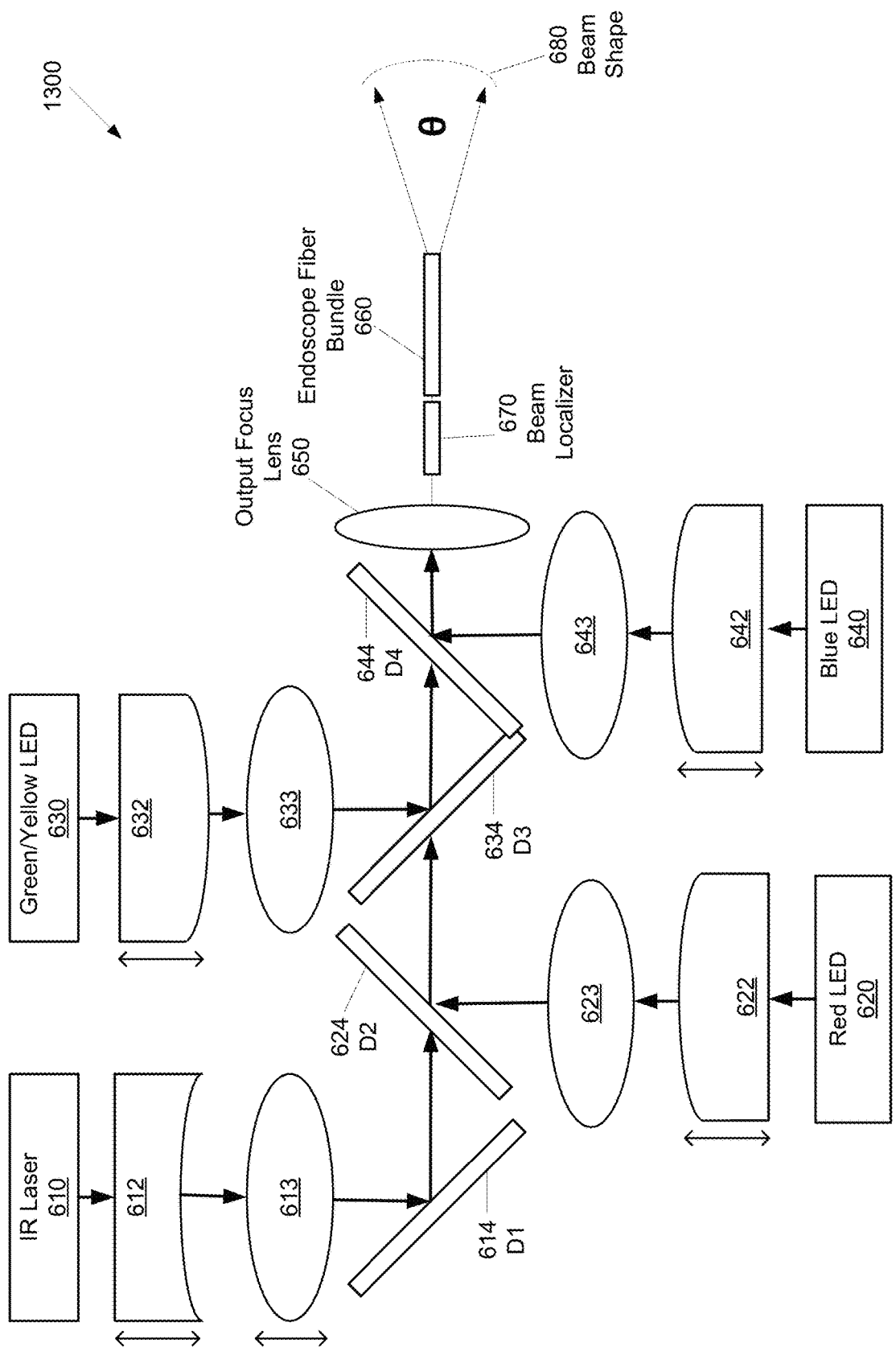
FIG. 13 is a schematic diagram of a first variation on the exemplary embodiment of FIG. 6, a hybrid laser and LED illumination source combining multiple color LEDs.

FIG. 13 shows a first exemplary variation 1300 of the first embodiment endoscope illumination system having a red LED 620 (610-650 nm), a blue LED 640 (430-470 nm) a green LED 630 (515-600 nm) and an IR laser 610 (785-800 nm) combined by using dichroic plates 614, 624, 634, 644. All three led beam angular profiles may be adjusted by using individual channel output beam shape adjustors 622, 632, 642. The IR laser beam distribution can be adjusted by using laser output beam shape adjustor 612 and beam angle adjuster 613 to adjust the output angular distribution.

Figure 14:
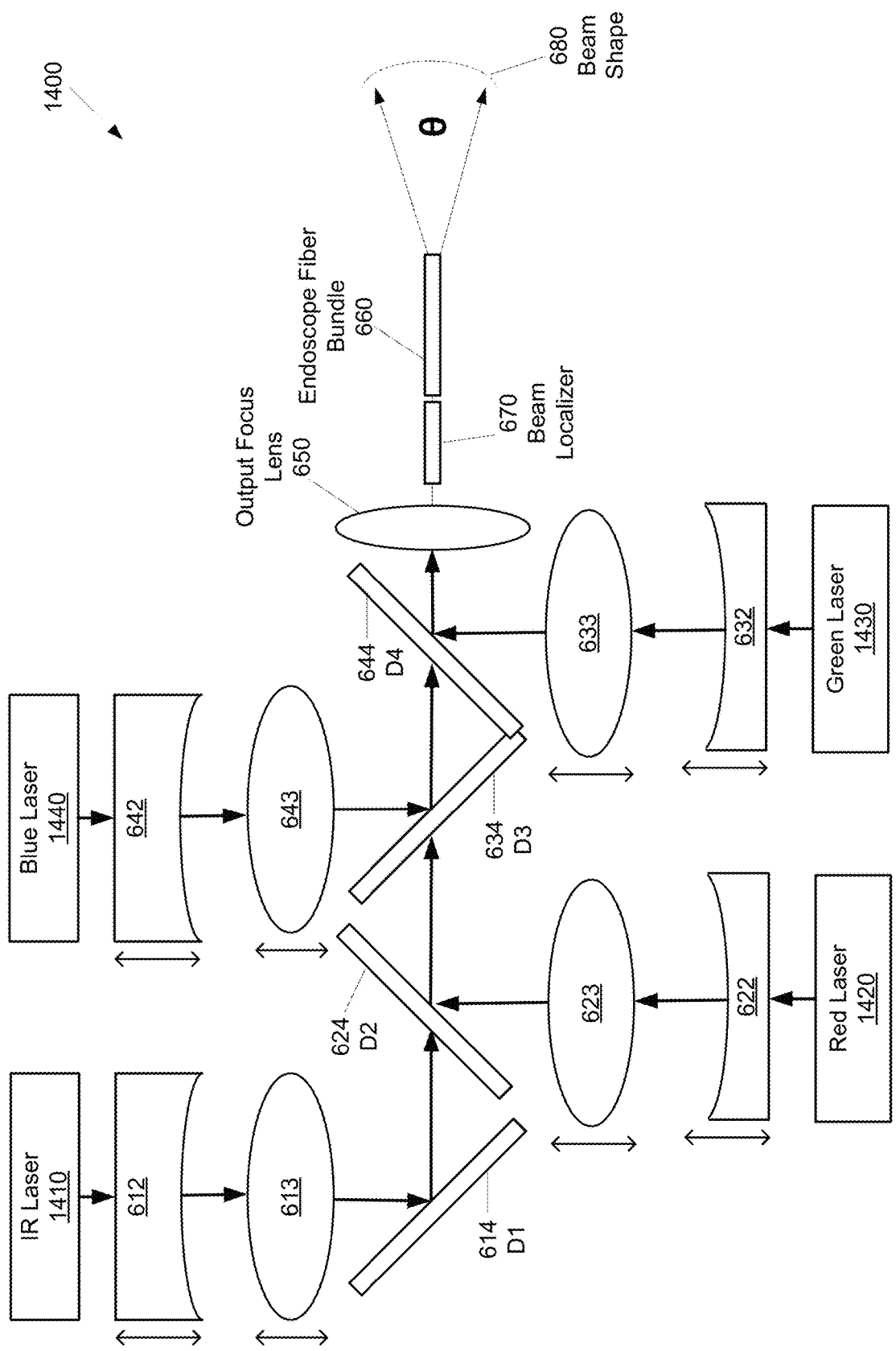
FIG. 14 is a schematic diagram of a second variation on the exemplary embodiment of FIG. 6, an illumination source combing all colors with laser sources.

FIG. 14 shows a second exemplary variation 1400 of the first embodiment endoscope illumination system having a red laser 1420 (635±5 nm), a blue laser 1440 (445±5 nm), a green laser 1430 (525 nm or 552 nm±5 nm), and an IR laser 1410 (797±5 nm). The four lasers 1410, 1420, 1430, 1440 are combined by using dichroic plates 614, 624, 634, 644. The angular distribution of all four beams can be adjusted by using individual channel beam shape adjustors 612, 622, 632, 642 to adjust the beam angular profiles and using beam angle adjusters 613, 623, 633, 643 to adjust the individual output angles.

Figure 15:
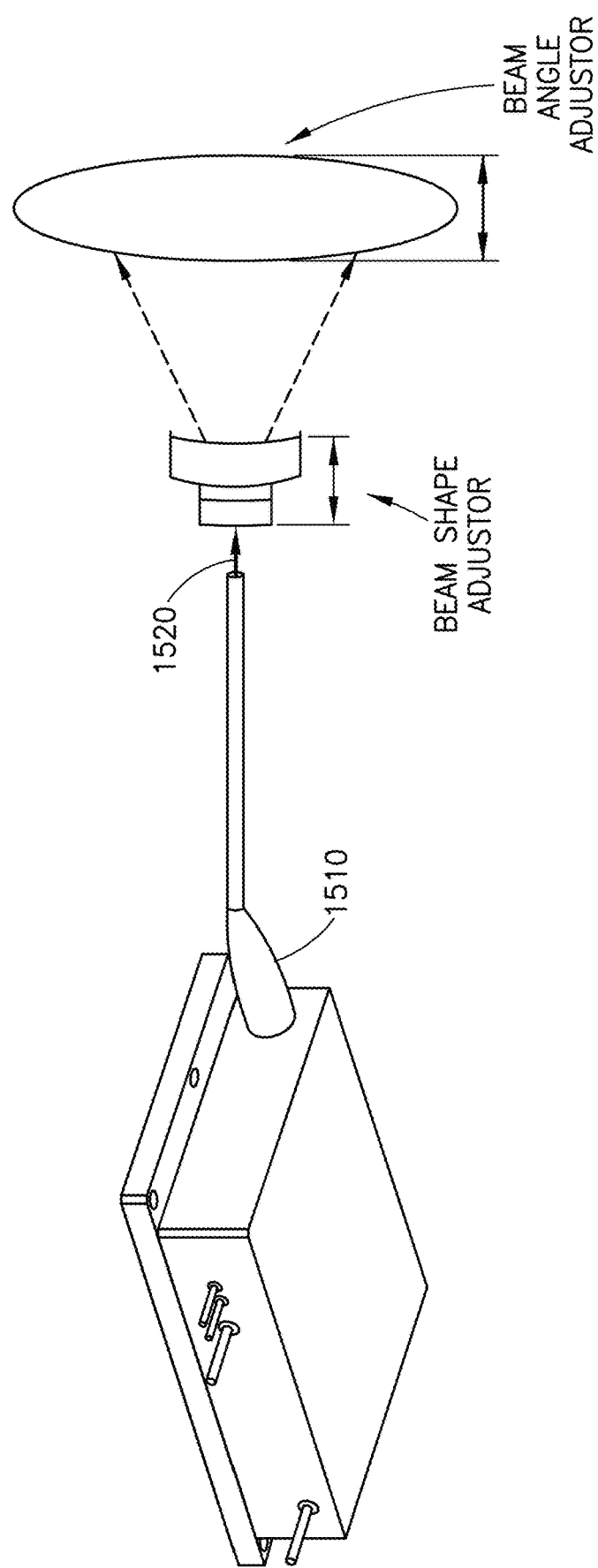
FIG. 15 is a schematic diagram of an exemplary endoscope illumination source where a plurality of lasers are fiber coupled.
Figure 16:
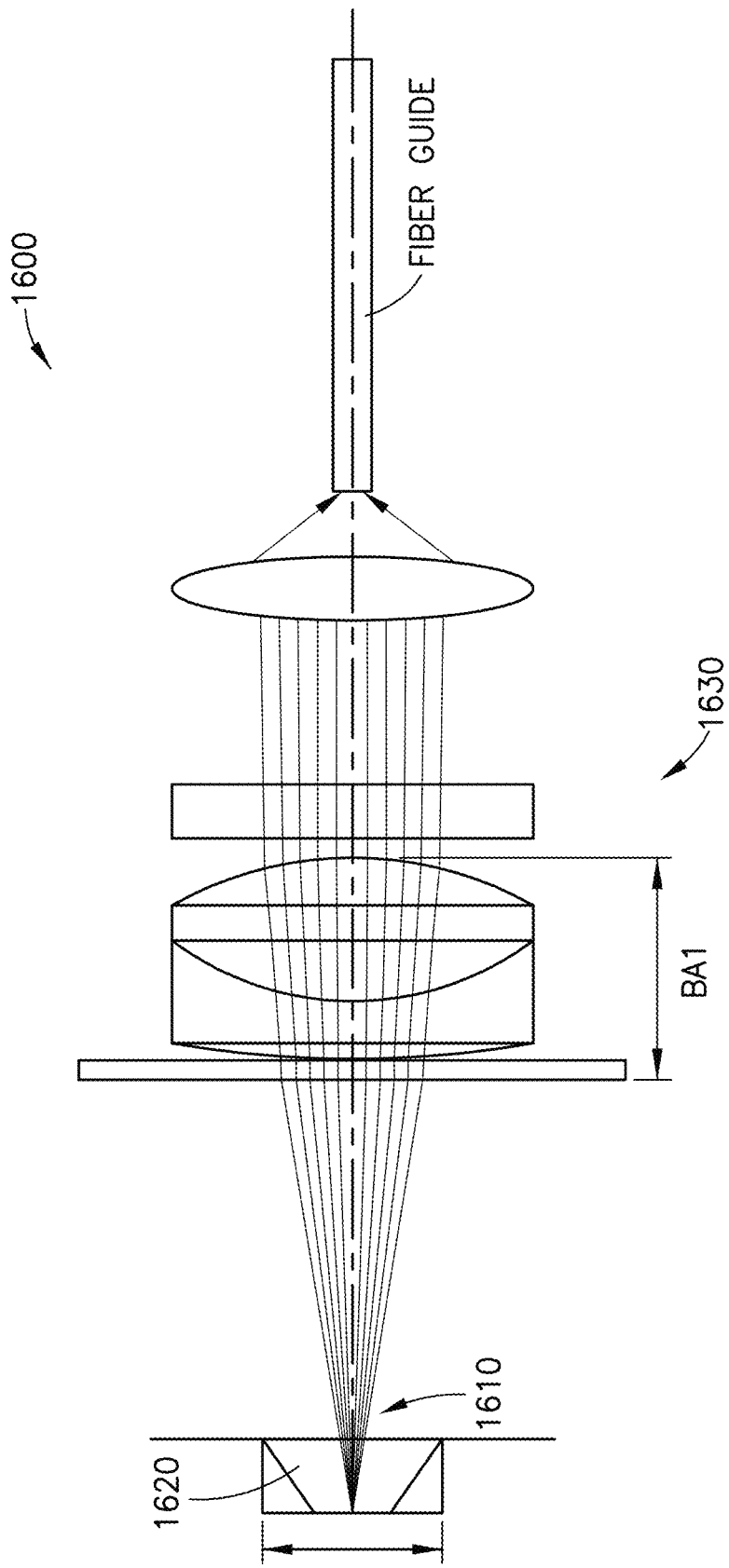
FIG. 16 is a schematic diagram of shows a second alternative embodiment of an endoscope illumination source.

It will be apparent to those skilled in the art that various modifications and variations can be made to the structure of the present invention without departing from the scope or spirit of the invention. For example, FIG. 15 shows an alternative embodiment 1500 of an endoscope illumination source where a plurality of lasers 1510 are fiber coupled, and a fiber output tip 1520 has a diffused surface to avoid producing a hot spot at an entrance of the endoscope. FIG. 16 shows an alternative embodiment 1600 of an endoscope illumination source where the LED source is mounted in a beam shape adjuster 1610 with cone scattering surface 1620 and a round opening. By adjusting the opening diameter, the output beam angular profile may be adjusted. Together with beam angle adjustor 1630, the output beam angular distribution may be adjusted. This may be useful when the beam angular distributions of the multiple sources are dissimilar. Here, the beam shape adjuster becomes a new beam formulator and adjustor. Other variations are also possible. For example, at least of the red, green, blue, and/or IR light assemblies may omit one or both of the output beam shape adjuster 612, 622, 632, 642 and the output beam angle adjuster 613, 623, 633, 643.

In view of the foregoing, it is intended that the present invention cover modifications and variations of this invention provided they fall within the scope of the following claims and their equivalents.

What is claimed is:

1. An illumination system for an endoscope comprising:
a plurality of light assemblies further comprising:
a red assembly comprising a red light source configured to emit a red beam with a wavelength in a range of 610-650 nm,
a blue assembly comprising a blue light source configured to emit a blue beam with a wavelength in a range of 430-470 nm;
a green assembly comprising a green light source configured to emit a green beam with a wavelength in a range of 515-600 nm; and
an infrared (IR) assembly comprising an IR light source configured to emit an IR beam with a wavelength in a range of 785-802 nm; and
a plurality of dichroic plates configured to combine output beams of the red assembly, the blue assembly, the green assembly, and the IR assembly, wherein the plurality of dichroic plates are co-axial with respect to one another, wherein each of the plurality of light assemblies further comprises:
an output beam shape adjuster configured to receive an output beam from the respective light source to adjust a respective output beam angular profile, wherein at least one parameter of the output beam shape adjuster is tunable, and
an output beam angle adjuster configured to receive a beam from the output beam shape adjuster and adjust a respective output beam angle, wherein at least one parameter of the output beam angle adjuster is tunable.

2. The illumination system of claim 1, wherein:
the red light source comprises a red light emitting diode (LED);
the blue light source comprises a blue LED; and
the green light source comprises a green LED.

3. The illumination system of claim 1, wherein the IR light source comprises an IR laser.

4. The illumination system of claim 1, wherein:
the red light source comprises a red laser configured to emit a red beam with a wavelength in a range of 630-640 nm;
the blue light source comprises a blue laser configured to emit a blue beam with a wavelength in a range of 440-450 nm;
the green light source comprises a green laser configured to emit a green beam with a wavelength in a range of 525-557 nm; and
the IR light source comprises an IR laser configured to emit a beam with a wavelength in a range of 792-802 nm.

5. The illumination system of claim 1, further comprising a beam localizer arranged to receive light from the plurality of dichroic plates.

6. The illumination system of claim 5, wherein the beam localizer comprises a homogenizing rod with a polygon cross-sectional profile shape.

7. The illumination system of claim 1, wherein the output beam shape adjuster of each of the plurality of light assemblies comprises one of the group consisting of a location adjustable positive lens, a location adjustable negative lens, and an opening adjustable scattering cone.

8. The illumination system of claim 1, wherein the beam angle adjuster of each of the plurality of light assemblies comprises one of the group consisting of a location adjustable positive lens and a location adjustable lens pair comprising a positive lens and a negative lens.

9. The illumination system of claim 1, wherein the IR laser source is configured for fiber coupling.

10. A method for providing illumination for an endoscope by a system comprising a plurality of dichroic plates and a plurality of light assemblies, each light assembly comprising a light source, an output beam shape adjuster, and an output beam angle adjusters, the method comprising the steps of:

for each light source of the plurality of light sources:
receiving an output beam by the output beam shape adjuster from the light source;
adjusting a parameter of the output beam shape adjuster;
receiving by the output beam angle adjuster the adjusted output beam angular profile from the output beam shape adjuster; and
adjusting a parameter of the output beam angle adjuster; and combining by the plurality of dichroic plates output beams of the plurality of light assemblies so that the output beams are co-axial with respect to one another, wherein the plurality of light assemblies further comprises:
a red assembly comprising a red light source configured to emit a red beam with a wavelength in a range of 610-650 nm,
a blue assembly comprising a blue light source configured to emit a blue beam with a wavelength in a range of 430-470 nm;
a green assembly comprising a green light source configured to emit a green beam with a wavelength in a range of 515-600 nm; and
an infrared (IR) assembly comprising an IR light source configured to emit an IR beam with a wavelength in a range of 785-802 nm.

11. An illumination system for an endoscope comprising:
a plurality of light assemblies further comprising:
a red assembly comprising a red light source configured to emit a red beam with a wavelength in a range of 610-650 nm,
a blue assembly comprising a blue light source configured to emit a blue beam with a wavelength in a range of 430-470 nm;
a green assembly comprising a green light source configured to emit a green beam with a wavelength in a range of 515-600 nm; and
an infrared (IR) assembly comprising an IR light source configured to emit an IR beam with a wavelength in a range of 785-802 nm; and
a plurality of dichroic plates configured to combine output beams of the red assembly, the blue assembly, the green assembly, and the IR assembly, wherein the plurality of dichroic plates are co-axial with respect to one another,
wherein at least one of the plurality of light assemblies comprises an output beam shape adjuster configured to receive an output beam from the respective red light source, blue light source, green light source, and IR light source to adjust a respective output beam angular profile, wherein at least one parameter of the output beam shape adjuster is tunable, and at least one of the plurality of light assemblies comprises an output beam angle adjuster configured to receive a beam from the at least one output beam shape adjuster and/or the respective red source, blue source, green source, and IR light source and adjust a respective output beam angle, wherein at least one parameter of the output beam angle adjuster is tunable.

12. The illumination system of claim 11, wherein:
the red light source comprises a red light emitting diode (LED);
the blue light source comprises a blue LED; and
the green light source comprises a green LED.

13. The illumination system of claim 11, wherein the IR light source comprises an IR laser.

14. The illumination system of claim 11, wherein:
the red light source comprises a red laser configured to emit a red beam with a wavelength in a range of 630-640 nm;
the blue light source comprises a blue laser configured to emit a blue beam with a wavelength in a range of 440-450 nm;
the green light source comprises a green laser configured to emit a green beam with a wavelength in a range of 525-557 nm; and
the IR light source comprises an IR laser configured to emit a beam with a wavelength in a range of 792-802 nm.

15. The illumination system of claim 11, further comprising a beam localizer arranged to receive light from the plurality of dichroic plates.

16. The illumination system of claim 15, wherein the beam localizer comprises a homogenizing rod with a polygon cross-sectional profile shape.

17. The illumination system of claim 11, wherein the at least one output beam shape adjuster comprises one of the group consisting of a location adjustable positive lens, a location adjustable negative lens, and an opening adjustable scattering cone.

18. The illumination system of claim 11, wherein the at least one beam angle adjuster comprises one of the group consisting of a location adjustable positive lens and a location adjustable lens pair comprising a positive lens and a negative lens.

19. The illumination system of claim 11, wherein the IR laser source further comprises a fiber output tip comprising a diffused surface configured to avoid a hot spot at an entrance of the endoscope.

20. The illumination system of claim 11, wherein:
the at least one tunable parameter of the output beam shape adjuster is a position of the output beam shape adjuster such that the position of the output beam shape adjuster is tunable, and
the at least one tunable parameter of the output beam angle adjuster is a position of the output beam angle adjuster such that the position of the output beam angle adjuster is tunable.

21. The illumination system of claim 1, wherein:
the at least one tunable parameter of the output beam shape adjuster is a position of the output beam shape adjuster such that the position of the output beam shape adjuster is tunable, and
the at least one tunable parameter of the output beam angle adjuster is a position of the output beam angle adjuster such that the position of the output beam angle adjuster is tunable.

* * * * *